US008962786B2

(12) United States Patent
Gunatillake et al.

(10) Patent No.: US 8,962,786 B2
(45) Date of Patent: *Feb. 24, 2015

(54) CHAIN EXTENDERS

(75) Inventors: Pathiraja Arachchillage Gunatillake, Mulgrave (AU); Timothy Graeme Moore, Braybrook (AU); Raju Adhikari, Wheelers Hill (AU)

(73) Assignee: PolyNovo Biomaterials Pty Ltd, Port Melbourne, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/164,316

(22) Filed: Jun. 20, 2011

(65) Prior Publication Data

US 2011/0287102 A1    Nov. 24, 2011

Related U.S. Application Data

(63) Continuation of application No. 11/992,340, filed as application No. PCT/AU2006/001380 on Sep. 20, 2006, now Pat. No. 7,964,696.

(30) Foreign Application Priority Data

Sep. 20, 2005    (AU) ................. 2005905192

(51) Int. Cl.
*C08G 18/00* (2006.01)
*C07C 69/675* (2006.01)
(Continued)

(52) U.S. Cl.
CPC .............. *C07C 69/675* (2013.01); *A61L 27/18* (2013.01); *A61L 31/06* (2013.01); *C07C 69/40* (2013.01);
(Continued)

(58) Field of Classification Search
USPC ............ 528/85, 44, 66, 75, 83; 560/179, 183
See application file for complete search history.

(56) References Cited

U.S. PATENT DOCUMENTS 3,007,899 A    11/1961    Urs
3,247,282 A     4/1966    Englisch
(Continued)

FOREIGN PATENT DOCUMENTS

EP    837084    4/1998
JP    07070296    3/1995
(Continued)

OTHER PUBLICATIONS

Ben-Shabat et al., "Synthesis and Characterization of Biodegradable Copolyesters and Copolyanhydrides Prepared from Fumaric and Succinic Acid Trimers and Oligomers," Israel Journal of Chemistry, vol. 45, 2005, pp. 411-420.
(Continued)

*Primary Examiner* — Michael L Leonard
(74) *Attorney, Agent, or Firm* — Novak Druce Connolly Bove + Quigg LLP (57) ABSTRACT

The present invention relates to chain extenders, processes for their preparation and their use in the preparation of biocompatible biodegradable polyurethanes and polyurethane ureas for biomedical applications such as stents, scaffolds for tissue engineering.

The chain extenders comprise a compound of formula(I)

16 Claims, 5 Drawing Sheets (51) Int. Cl.
*A61L 27/18* (2006.01)
*A61L 31/06* (2006.01)
*C07C 69/40* (2006.01)
*C07C 69/60* (2006.01)
*C08G 18/10* (2006.01)
*C08G 18/32* (2006.01)
*C08G 18/42* (2006.01)
*C08G 18/66* (2006.01)
*C08G 18/77* (2006.01)

(52) U.S. Cl.
CPC ............... *C07C 69/60* (2013.01); *C08G 18/10* (2013.01); *C08G 18/3221* (2013.01); *C08G 18/4277* (2013.01); *C08G 18/664* (2013.01); *C08G 18/6674* (2013.01); *C08G 18/771* (2013.01)
USPC .................. 528/83; 528/44; 528/66; 528/75; 528/85

(56) References Cited

U.S. PATENT DOCUMENTS

| | | | |
|---|---|---|---|
| 3,281,378 A | 10/1966 | Garber at al. | |
| 3,360,546 A | 12/1967 | Wygant at al. | |
| 4,035,274 A | 7/1977 | McGinniss | |
| 4,116,741 A | 9/1978 | Thoma et al. | |
| 4,192,827 A | 3/1980 | Mueller et al. | |
| 4,273,690 A | 6/1981 | Walus | |
| 4,284,506 A | 8/1981 | Tetenbaum et al. | |
| 4,293,679 A | 10/1981 | Cogliano | |
| 4,412,033 A | 10/1983 | LaBelle et al. | |
| 4,424,252 A | 1/1984 | Nativi | |
| 4,451,523 A | 5/1984 | Nativi et al. | |
| 4,908,406 A | 3/1990 | Mulhaupt et al. | |
| 4,935,480 A | 6/1990 | Zdrahala et al. | |
| 5,041,516 A | 8/1991 | Frechet et al. | |
| 5,109,077 A | 4/1992 | Wick | |
| 5,276,068 A | 1/1994 | Waknine | |
| 5,578,662 A | 11/1996 | Bennett et al. | |
| 5,886,127 A | 3/1999 | Newkome et al. | |
| 5,981,684 A | 11/1999 | Bruchmann et al. | |
| 6,124,370 A | 9/2000 | Walton et al. | |
| 6,150,438 A | 11/2000 | Shiraishi et al. | |
| 6,372,876 B1 | 4/2002 | Kim et al. | |
| 6,376,637 B1 | 4/2002 | Bruchmann et al. | |
| 6,376,742 B1 | 4/2002 | Zdrahala et al. | |
| 6,388,047 B1 | 5/2002 | Won et al. | |
| 6,753,384 B2 * | 6/2004 | Whitehouse et al. | 525/415 |
| 7,799,874 B2 * | 9/2010 | Carr et al. | 525/415 |
| 2001/0005738 A1 | 6/2001 | Bruchmann et al. | |
| 2002/0103347 A1 | 8/2002 | Isaka et al. | |
| 2003/0153673 A1 | 8/2003 | Schwalm et al. | |
| 2004/0097684 A1 | 5/2004 | Bruchmann et al. | |
| 2005/0013793 A1* | 1/2005 | Beckman et al. | 424/78.27 |
| 2005/0112203 A1 | 5/2005 | Shau et al. | |
| 2006/0051394 A1 | 3/2006 | Moore et al. | |
| 2006/0074208 A1 | 4/2006 | Laredo | |
| 2006/0216323 A1* | 9/2006 | Knaack et al. | 424/422 |
| 2008/0262613 A1 | 10/2008 | Gogolewski | |
| 2009/0099600 A1* | 4/2009 | Moore et al. | 606/246 |

FOREIGN PATENT DOCUMENTS

| | | |
|---|---|---|
| WO | WO-9902168 | 1/1999 |
| WO | WO-0012579 | 3/2000 |
| WO | WO-0067813 | 11/2000 |
| WO | WO-0210247 | 2/2002 |
| WO | WO-0210292 | 2/2002 |
| WO | WO-2004065450 | 8/2004 |
| WO | WO-2005089778 | 9/2005 |
| WO | WO-2006010278 | 2/2006 |

OTHER PUBLICATIONS

Office Action received in EP 03739861.7 dated Jan. 18, 2008 (Polynovo Biomaterials Pty Ltd.).
Restriction Requirement dated Apr. 2, 2009 (Polynovo Biomaterials Pty Ltd. U.S. Appl. No. 11/087,561).
Restriction Requirement dated Nov. 28, 2007 (Polynovo Biomaterials Pty Ltd. U.S. Appl. No. 11/070,217).
Response dated Dec. 26, 2007 (Polynovo Biomaterials Pty Ltd. U.S. Appl. No. 11/070,217).
Non-Final Office Action dated Mar. 27, 2008 (Polynovo Biomaterials Pty Ltd. U.S. Appl. No. 11/070,217).
Response dated Jul. 28, 2008 (Polynovo Biomaterials Pty Ltd. U.S. Appl. No. 11/070,217).
Final Rejection dated Oct. 30, 2008 (Polynovo Biomaterials Pty Ltd. U.S. Appl. No. 11/070,217).
Response to Final Office Action dated Jan. 30, 2009 (Polynovo Biomaterials Pty Ltd. U.S. Appl. No. 11/070,217).
Advisory Action dated Mar. 21, 2009 (Polynovo Biomaterials Pty Ltd. U.S. Appl. No. 11/070,217).
Preliminary Amendment dated Sep. 25, 2006 (Polynovo Biomaterials Pty Ltd. U.S. Appl. No. 10/520,414).
Restriction Requirement dated Sep. 12, 2007 (Polynovo Biomaterials Pty Ltd. U.S. Appl. No. 10/520,414).
Response dated Oct. 12, 2007 (Polynovo Biomaterials Pty Ltd. U.S. Appl. No. 10/520,414).
Non-Final Action dated Nov. 29, 2007 (Polynovo Biomaterials Pty Ltd. U.S. Appl. No. 10/520,414).
Response to Non-Final Action dated Feb. 29, 2008 (Polynovo Biomaterials Pty Ltd. U.S. Appl. No. 10/520,414).
Final Office Action dated May 29, 2008 (Polynovo Biomaterials Pty Ltd. U.S. Appl. No. 10/520,414).
Response to Final Office Action dated Nov. 12, 2008 (Polynovo Biomaterials Pty Ltd. U.S. Appl. No. 10/520,414).
Office Action dated Feb. 3, 2009 (Polynovo Biomaterials Pty Ltd. U.S. Appl. No. 10/520,414).
Arroyo et al. Revista de Plasticos Modernos, 218:217-226, 1974.
Yoshida et al. Agricultural and Biological Chemistry 34(11).1668-1675.
Ogata et al., Biochemica et Biophysica Acta, 742:384-390, 1983.
STN Database, File Registry, Registry No. 57214-23-0.
STN Database, File CA, Accession No. AN 82:113308.

* cited by examiner

CHAIN EXTENDERS

CROSS REFERENCE TO RELATED APPLICATIONS

This application is a continuation application of application Ser. No. 11/992,340, now U.S. Pat. No. 7,964,696 which is a National Phase filing under 35 U.S.C. §371 of PCT/AU2006/001380, filed on Sep. 20, 2006, which claims priority to Australian Patent Application No. 2005905192, filed on Sep. 20, 2005; the entire contents of all are hereby incorporated by reference.

FIELD

The present invention relates to chain extenders, processes for their preparation and their use in the preparation of biocompatible biodegradable polyurethanes and polyurethane ureas for biomedical applications such as stents, orthopaedic fixation scaffolds and scaffolds for tissue engineering.

BACKGROUND

Biodegradable polyurethanes and polyurethane ureas are typically formulated using polyester polyols, aliphatic diisocyanates and diol or diamine chain extenders. The polyester polyol forms the 'soft' segment of the polymer while the diisocyanate and the chain extender form the hard segment. The hard segment forms ordered domains due to hydrogen bonding and imparts high mechanical strength to the material. The soft domains are formed largely by the polyester polyol and provides elastic properties to the polymer. Polyester polyols such as polycaprolactone, polyglycolide and polylactide are the most widely used polyols in biodegradable polyurethanes. The biodegradation of these polymers occur largely due to the hydrolytic degradation of the ester, urethane and urea linkages of the polymer. The soft segment of the polyurethane degrades significantly faster than the hard segment. This is largely due to the presence of relatively easily hydrolysable ester linkages and the amorphous nature of the soft segment. The hard segment of biodegradable polyurethanes is formed from diisocyanates such as hexamethylene diisocyanate (HDI), butane diisocyanate (BDI), lysine diisocyanate ethyl ester and lysine diisocyanate methyl ester. The chain extenders are low molecular weight (typically MW<400) diols or diamines. Examples include 1,4-butanediol, ethylene glycol, ethylene diamine and water. The diols and diisocyanates react to form urethane linkages in the hard segment of the polyurethane. The diamine chain extenders and water react to form urea linkages. The urethane or urea linkages in the hard segment also degrade by hydrolysis but at a significantly slower rate than ester linkages.

An important consideration in the design of biodegradable polymers is the choice of precursors that would lead to polyurethanes with backbone functional groups susceptible to one or more degradation pathways in the body, such as hydrolytic or enzymatic degradation. Such polyurethanes degrade to low molecular weight products which are either bioresorbed or released from the body through one of the waste disposal pathways in the body. The use of conventional diisocyanates and chain extenders such as ethylene glycol or ethylene diamine leads to polyurethane with hard segments with urethane, urea or a combination of such functional groups. Because of the relatively slow degradation rates of these linkages compared with ester linkages, the polymer degradation may lead to oligomers containing mainly hard segments. This becomes a major concern, particularly when polyurethanes are formulated with a higher percentage of hard segment (longer hard segment lengths). Accordingly, it is desirable if the hard segments also break down rapidly to low molecular weight compounds for rapid release from the body. This also broadens the formulation options for the design of biodegradable polyurethanes with degradation rates tailored to specific applications.

Chain extenders which break down to biocompatible compounds such as amino acids have been used for formulating biodegradable polyurethanes. The chain extenders are diamines based on cyclohexane dimethanol and phenyl alanine and are generally too high in molecular weight (MW 438) to be considered as chain extenders. The high molecular weight combined with the bulky benzyl pendant groups leads to polyurethanes with disrupted hard segments, limiting the range of properties that can be achieved using such chain extenders in polyurethanes.

SUMMARY

The present invention relates to chain extenders with one or more hydrolysable (degradable) functional groups in the backbone.

The chain extenders are based on ester diols of hydroxy acids or dicarboxylic acids which optionally contain a free radically polymerisable functional group(s) in the backbone.

According to one aspect of the present invention there is provided a chain extender comprising a compound of formula (I):

in which
r, s, t, u and v are independently 0 or 1 provided that at least two of r, s, t, u and v are 1;
X and $X_1$ are O, S or NR in which R is H or optionally substituted $C_{1-6}$alkyl;
$R_1$, $R_2$ and $R_3$ are independently selected from optionally substituted $C_{1-20}$ alkylene and optionally substituted $C_{2-20}$ alkenylene both of which may be optionally interrupted by optionally substituted aryl or optionally substituted heterocyclyl.

In a preferred embodiment there is provided a chain extender comprising a compound of formula (I) in which
r, s, t, and u are Independently 0 or 1, v is 0, provided that at least two of r, s, t, and u are 1 and that at least one of s or t is 1;
$X_1$ is O, S or NR in which R is H or optionally substituted $C_{1-6}$ alkyl;
X is O or S;
$R_1$, $R_2$ and $R_3$ are independently selected from optionally substituted $C_{1-20}$ alkylene and optionally substituted $C_{2-20}$ alkenylene both of which may be optionally interrupted by optionally substituted aryl or optionally substituted heterocyclyl.

According to another aspect of the present invention, there is provided a chain extender of formula (I) defined above provided that when r and s are 1, t, u and v are 0, X is O and $R_2$ is $(CH_2)_2$. then $R_1$ is not $CH_2$, $CHCH_3$ or $(CH_2)_3$ (GA-EG, LA-EG or EG-4HB).

Examples of compounds covered by formula (I) are shown in the following table:

|  | r | s | t | u | v |
|---|---|---|---|---|---|
| Dimer diol | 1 | 1 | 0 | 0 | 0 |
| Trimer diol | 1 | 0 | 1 | 1 | 0 |
| Dimer acid | 0 | 1 | 1 | 0 | 0 |
| Trimer acid | 0 | 0 | 1 | 1 | 1 |
| Dimer hydroxy acid | 0 | 0 | 1 | 1 | 0 |

The present invention also provides use of the compound of formula (I) defined above as a chain extender.

The present invention further provides the compound of formula (I) as defined above when used as a chain extender.

Some of the compounds of formula (I) are novel per se .and form part of the invention such as z-caprolactone and ethylene.glycol dimer (CL-EG).

The present invention also provides a process for the preparation of the compound of formula (I) defined above which comprises the step of transesterification of a compound Of formula (II) or (III):

in which $R_2$ is as defined above and n is an integer from 1 to 50, with a compound of formula (IV)

HOR¹OH (IV)

in which $R_1$ is as defined above.

It will be appreciated that the compound of formula (I) may be used in combination with a conventional chain extender.

According to another aspect of the present invention there is provided a chain extender composition comprising the compound formula (I) defined above and a conventional chain extender.

The chain extender and chain extender composition are particularly useful in preparing biocompatible biodegradable polyurethane or polyurethane ureas for biomedical applications.

According to a still further aspect of the present invention there is provided a biocompatible biodegradable polyurethane or polyurethane urea comprising a segment formed from the chain extender or chain extender composition defined above.

In one embodiment the biocompatible biodegradable polyurethane or polyurethane urea comprises a reaction product of an isocyanate, polyol and the chain extender or chain extender composition defined above.

In another embodiment, the biocompatible biodegradable polyurethane or polyurethane urea may also be prepared using only an isocyanate and a chain extender or chain extender composition defined above. The chain extender in this instance has a dual functionality as both a chain extender and a polyol.

The biocompatible biodegradable polyurethanes or polyurethane ureas are particularly useful as scaffolds for coronary artery, blood vessels or cardiac tissue, wound repair, plastic or cosmetic surgery, nerve regeneration, spinal disc repair or augmentation, orthopaedic or tissue engineering applications.

Thus, the present invention also provides a biocompatible biodegradable polymeric scaffold comprising a cross-linked or linear polyurethane or polyurethane urea as defined above.

In one embodiment, the scaffold is a stent; stent coating; bone substitute; bone filler; bone cement; an orthopaedic fixation scaffold such as a screw, pin, plate or spinal cage or a dart arrow, pin or adhesive for soft tissue repair including meniscal and articular cartilage, tendons ligaments and connective tissue; or a filler for vertobroplasty or kyphoplasty.

The present invention further provides a medical device or composition which is wholly or partly composed of the scaffold defined above.

DETAILED DESCRIPTION

Chain Extender

The term "chain extender" refers to a lower molecular weight compound having two or more functional groups that are reactive towards isocyanate and having a molecular weight of less than 400.

The chain extenders of the present invention have one or more hydrolysable (degradable) functional groups in the backbone. The term "hydrolysable (degradable) functional group" refers to any molecular moiety which may be part of the chain extender and is preferably biocompatible and bioresorbable on in vivo degradation of the biocompatible biodegradable polyurethane or polyurethane urea which is formed from the chain extender.

The chain extenders of the present invention are based on ester diols of α-hydroxy acids or dicarboxylic acids which optionally contain free radically polymerisable functional group(s) in the backbone. When these chain extenders are used either alone or in combination with conventional chain extenders to form polyurethanes or polyurethane ureas, the polyurethanes degrade at faster rates than those based on conventional chain extenders. Furthermore, the polyurethanes or polyurethane ureas degrade to low molecular weight compounds due to the degradation of the hard segment which is formed from the chain extenders of the present invention at rates comparable to that of the soft segment which results in minimum levels of oligomeric hard segment species among the degradation products. The chain extenders based on ester diols of dicarboxylic acids provide two hydrolysable (degradable) functional groups within the chain extender backbone to facilitate even faster break down of the hard segment structure. The presence of a free radically poymerisable functional group in the backbone also facilitates cross linking of the hard segment. Polyurethanes or polyurethane ureas based on these chain extenders can be processed and subsequently cross linked to form network structures with improved mechanical properties.

Preferred chain extenders of formula (I) have the formula (Ia) and (Ib) shown below.

in which $R_1$ to $R_3$ are as defined above, preferably optionally substituted $C_{1-6}$ alkylene or optionally substituted $C_2$ alkenylene.

In certain embodiments, at least one of the substituents of the $C_{1-20}$ alkylene or $C_{2-20}$ alkenylene groups of $R_1$, $R_2$ or $R_3$ comprises a bioactive moiety.

In other embodiments, at least one of the substituents of the $C_{1-20}$ alkylene or $C_{2-20}$ alkenylene groups of $R_1$, $R_2$ or $R_3$ comprises an ester, amide, thiol, anhydride, imide, carbonate, peroxide, peroxyester, phosphate ester, thioester, sulphate ester, carbamate or azo moiety.

In some instances, the ester, amide, thiol, anhydride, imide, carbonate, peroxide, peroxyester, phosphate ester, thioester, sulphate ester, carbamate or azo moiety is located between a bioactive moiety and the backbone of the chain extender.

In some embodiments, at least one of $R_1$, $R_2$ or $R_3$ comprises 5-alpha-reductase inhibitors, amebicides, aminosalicylates, anaesthetics (general and local), analgesics, angiogenesis inhibitors, angiotensin inhibitors, anorexiants, antianginal agents, antiarrhythmic agents, antiarthritic agents, anticoagulants, anticonvulsants, antidepressants, antiemetics, antihistamines, antihyperlipidemic agents, antihypertensives, antiinfectives, anti-inflammatories, antimalarial, antimetabolites, antimicrobial, antimigraine, antiparasitic agents, antiparkinson agents, antiprotozoal agents, antipsychotics, antitussives, antiulcer agents, antivirals, anxiolytics, beta-adrenergic blocking agents, bisphosphonates, bronchodilators, calcium channel blockers, cancer therapeutics, carbonic anhydrase inhibitors, cardiovascular pharmaceuticals, central nervous system pharmaceuticals, chemokine receptor antagonist, contraceptives, coumarins, cox-2 inhibitors, cytotoxics, decongestants, expectorants, diabetes therapies, diuretics, fertility pharmaceuticals, growth agents, growth promoters, H2 antagonists, hematinics, hemostatics, heparin antagonists, hormones and analogs, immunostimulants, immunosuppressants, impotence agents, indandiones, inotropic agents, kinase inhibitors, leukotriene modifiers, macrolides, mast cell stabilizers, mitotic inhibitors, muscle relaxants, muscle stimulants, mydriatics, neuromuscular blocking agents, obesity therapeutics ophthalmic pharmaceuticals, osteoporosis drugs, peptides, platelet inhibitors, platelet stimulating agents, prolactin inhibitors, protease inhibitors, proton pump inhibitors, psychoactive drugs, radiopharmaceuticals, respiratory pharmaceuticals, sedatives, smoking cessation agents, spermicides, statins, steroids, stimulants, sulphonamides, thyroid drugs, tranquilisers, vasodilators or vitamins.

In certain embodiments, when R1, R2, or R3 is an optionally substituted heterocyclyl group the heterocyclyl group comprises a fluoroquinolone. For example, the heterocyclyl group may be selected from the group consisting of:

Alatrofloxacin

Balofloxacin

Ciprofloxacin

Clinafloxacin

Danofloxacin

Delafloxacin

Dextrofloxacin

Difloxacin

Enoxacin

Enrofloxacin

Garenoxacin

Gatifloxacin

Gemifloxacin

Grepafloxacin

Levofloxacin

Lomefloxacin

Marbofloxacin

Moxifloxacin

-continued

Nadifloxacin

Norfloxacin

Ofloxacin

Orbifloxacin

Pefloxacin

Sitafloxacin

-continued

Sparfloxacin

Temafloxacin

Tosufloxacin

Trovafloxacin

Amifloxacin

Representative examples of a compound of formula (Ia) are as follows:

6-hydroxy-hexanoic acid 2-hydroxyethyl ester (CL-EG)

6-hydroxy-hexanoic acid 4-hydroxybutyl ester (CL-BDO)

Representative examples of a compound of formula (Ib) are as follows:

Ethylene glycol succinic acid diester diol (EG-Suc-EG)
(Succinic acid bis-(2-hydroxy-ethyl) ester)

Ethylene glycol fumaric acid diester diol (EG-Fum-EG)
(Trans-but-2-enedioic acid bis-(2-hydroxy-ethyl) ester)

The terms "$C_{1-20}$ alkylene" and "$C_{2-20}$ alkenylene" are the divalent radical equivalents of the terms "$C_{1-20}$ alkyl" and "$C_{2-20}$ alkenyl" respectively. The two bonds connecting the alkylene or alkenylene to the adjacent groups may come from the same carbon atom or different carbon atoms in the divalent radical.

The term "$C_{1-20}$ alkyl" refers to linear, branched or cyclic hydrocarbon groups having from 1 to 20 carbon atoms, preferably from 1 to 6 carbon atoms. Illustrative of such alkyl groups are methyl, ethyl, propyl, isopropyl, butyl, sec-butyl, tert-butyl, pentyl, neopentyl, hexyl, cyclopropyl, cyclobutyl, cyclopentyl or cyclohexyl.

The term "alkenyl" refers to linear or branched hydrocarbon groups having at least one carbon—carbon double bond of 2 to 20 carbon atoms, preferably from 2 to 6 carbon atoms. Examples of alkenyl include ethenyl, propenyl, allyl, propenyl, butenyl and 4-methylbutenyl.

The term "aryl" refers to a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl.

The term "heterocyclyl" refers to saturated or unsaturated, monocyclic or polycyclic hydrocarbon group containing at least one heteroatom selected from nitrogen, sulphur and oxygen Suitable heterocyclic groups include N-containing heterocyclic groups, such as, unsaturated 3 to 6-membered heteromonocyclic groups . containing 1 to 4 nitrogen atoms, for example, pyrrolyl, pyrrolinyl, imidazolyl, pyrazolyl, pyridyl, pyrimidinyl, pyrazinyl, pyridazinyl, triazolyl or tetrazolyl;

saturated 3 to 6-membered heteromonocyclic groups containing 1 to 4 nitrogen atoms, such as, pyrrolidinyl, imidazolidinyl, piperidino or piperazinyl;

unsaturated condensed heterocyclic groups containing 1 to 5 nitrogen atoms, such as indolyl, isoindolyl, indolizinyl, benzimidazolyl, quinolyl, isoquinolyl, indazolyl, benzotriazolyl or tetrazolopyridazinyl;

unsaturated 3 to 6-membered heteromonocyclic group containing an oxygen atom, such as, pyranyl or furyl;

unsaturated 3 to 6-membered heteromonocyclic group containing 1 to 2 sulphur atoms, such as, thienyl;

unsaturated 3 to 6-membered heteromonocyclic group containing 1 to 2 oxygen atoms and 1 to 3 nitrogen atoms, such as, oxazolyl, isoxazolyl or oxadiazolyl;

saturated 3 to 6-membered heteromonocyclic group containing 1 to 2 oxygen atoms and 1 to 3 nitrogen atoms, such as, morpholinyl;

unsaturated condensed heterocyclic group containing 1 to 2 oxygen atoms and 1 to 3 nitrogen atoms, such as, benzoxazolyl or benzoxadiazolyl;

unsaturated 3 to 6-membered heteromonocyclic group containing 1 to 2 sulphur atoms and 1 to 3 nitrogen atoms, such as, thiazolyl or thiadiazolyl;

saturated 3 to 6-membered heteromonocyclic group containing 1 to 2 sulphur atoms and 1 to 3 nitrogen atoms, such as, thiazolidinyl; and unsaturated condensed heterocyclic group containing 1 to 2 sulphur atoms and 1 to 3 nitrogen atoms, such as, benzothiazolyl or benzothiadiazolyl.

The term "optionally substituted" refers to a group may or may not be further substituted with one or more groups selected from $C_{1-6}$ alkyl, $C_{2-6}$ alkenyl, $C_{2-6}$ alkynyl, aryl, halo, halo $C_{1-6}$alkyl, halo $C_{2-6}$alkenyl, halo$C_{2-6}$alkynyl, haloaryl, hydroxy, $C_{1-6}$alkoxy, $C_{2-6}$alkenyloxy, $C_{1-6}$aryloxy, benzyloxy, halo $C_{1-6}$alkoxy, haloalkenyloxy, haloaryloxy, nitro, nitro$C_{1-6}$alkyl, nitro$C_{2-6}$alkenyl, nitro$C_{2-6}$alkynyl, nitroaryl, nitroheterocyclyl, amino, $C_{1-6}$alkylamino, $C_{1-6}$dialkylamino, $C_{2-6}$alkenylamino, $C_{2-6}$alkynyfamino, arylamino, diarylamino, benzylamino, dibenzylamino, acyl, alkenylacyl, alkynylacyl, arylacyl, acylamino, diacylamino, acyloxy, $C_{1-6}$alkylsulphonyloxy, arylsulphenyloxy, heterocyclyl, heterocyclyloxy, heterocyclylamino, haloheterocyclyl, $C_{1-6}$ alkylsulphenyl, arylsuiphenyl, carboalkoxy, carboaryloxy, mercapto, $C_{1-6}$alkylthio, benzylthio, acylthio, phosphorus-containing groups and the like. Preferred optional substituents are methyl, ethyl, propyl, butyl, and phenyl.

Process

The chain extenders may be prepared by transesterification of an α-hydroxy acid or dicarboxylic acid polymer of formula (II) with an alkane diol of formula (III) which is preferably present in an excess amount. Examples of α-hydroxy hydroxy acids Include glycolic acid, L-Lactic acid, D,L-lactic acid, 3-hydroxy propionic acid, 4-hydroxy, butyric acid, 3-hydroxy butyric acid and 5-hydroxy pentanoic acid. Examples of dicarboxylic acids include succinic acid, fumaric and maleic acid. Examples of alkane diols ,Include ethylene glycol, propylene glycol, butane diol, pentane diol and hexane diol. The chain extender prepared by this process may then be purified using any suitable known technique such as fractional distillation, solvent fractionation, chromatographic separation such as preparative gel permeation or high performance liquid chromatography.

Chain Extender Composition

The conventional chain extender is preferably difunctional and may be diols, dithiois, diamines, amino acids or dicarboxylic acids. Examples include dials such as ethylene glycol, diethylene glycol, tetraethylene glycol, 1,3-propane diol, 1,4-butane diol and 1,6-hexane diol; diamines such as butane diamine, ethanolamine, glycine and lysine; and dithiols such as alkyldithiols, i.e. ethane or propane dithlol.

Polyurethane or Polyurethane Ureas

The biocompatible biodegradable polyurethanes or polyurethane ureas of the present invention are preferably prepared by reacting an isocyanate, polyol and the chain extender or chain extender composition defined above.

Preferably the polyurethanes or polyurethane ureas are thermoplastic and of the general formula:

in which $R_x$ is from the isocyanate, $R_y$ is from the chain extender and $R_z$ is from the soft segment polyol. The pronumeral 'q' represents the average number of repeat units in the hard segment. The pronumeral 'r' represents the average number of repeat units in the soft segment. The pronumeral 's' is proportional to the molecular weight of the polymer and includes both the hard segments repeat units and the soft segment. 'q' is an integer between 1 and 100; 'r' is an integer between 0 and 100, and 's' is an integer between 1 and 500.

Isocyanates suitable for preparation of the polyurethanes or polyurethane ureas of the invention are those which are selected from the group consisting of optionally substituted aliphatic, aromatic and hindered isocyanates or isothiocyanates. Preferably the isocyanate is a diisocyanate.

Examples include isophorone diisocyanate, cyclohexane diisocyanate and the following:

MLDI - lysine diisocyanate methyl ester

ELDI - lysine diisocyanate ethyl ester

BDI - Butane diisocyanate

HDI - hexamethylene diisocyanate

H$_{12}$MDI - 4,4-methylene-bis(cyclohexyl isocyanate)

Dicyclohexylmethane diiso(thio) cyanate

-continued

Butanediiso(thio)cyanate

-continued

Hexane diiso(thio)cyanate

The term "polyol" refers to a molecule which has at least two or more functional hydroxyl groups that can react with isocyanate groups to form urethane groups. Examples of polyols include but are not limited to diols, triols, and macromers such as macrodiols. Preferably the polyol has a molecular weight of 200-5000, more preferably 200-2000, and even more preferably 200-1000. The polyol may be terminated by, for example, a hydroxyl, thiol or carboxylic acid group.

The structure of the polyol is preferably:

in which h and/or k can equal 0 (as is the case of the dimer, eg, h=0, j=1 and k=1) or are integers as is j and $R^4$ and $R^7$ are independently selected from hydrogen, hydroxyl, alkyl, aminoalkyl, (both primary and secondary) and carboxy alkyl and $R^6$ and $R^5$ cannot be hydrogen, but can independently be a linear or branched alkyl, alkenyl, aminoalkyl, alkoxy or aryl. The molecular weight of the entire structure is preferably 120 to 400. Less preferably the molecular weight can be up to 2000 and much less preferably above 2000. Four examples of suitable soft segments are as follows:

Poly(ε-caprolactone) diol, MW 400: in which $R^6$ is ($CH_2$—$CH_2$), $R^5$ is ($CH_2$)$_5$, $R^4$ and $R^7$ are both H, and j=1 and (h+k)=2.96

(Glycolic acid-ethylene glycol) dimer: in which $R^6$ is ($CH_2$—$CH_2$), $R^5$ is ($CH_2$), $R^4$ and $R^7$ are both H, j=1 and (h+k)=1

Poly(ethylene glycol), MW 400: in which h=0, k=0, j=~13, $R^6$ is ($CH_2$—$CH_2$), $R^4$ and $R^7$ are both H Poly(ethylene glycol) bis(3-aminopropyl) terminated (Aldrich); in which R is ($CH_2$—$CH_2$), $R^4$ and $R^7$ are both —($CH_2$)$_2$$NH_2$, j=34 and (h+k)=0

Either or both $R^6$ and $R^7$ can contain nonlinear structures, for example where R'=($CH_2CHCH_3$) which is lactic acid. However, the $R^6$ and $R^7$ should preferably not contain groups such as OH and $NH_2$ which are likely to cause crosslinking. Suitable compounds include but are not limited to the following polyester polyols:

PGA-Poly-(glycolic acid) diol,
in which R is typically
——(CH₂CH₂)——

PLA-Poly-(lactic acid) diol,
in which R is typically
——(CH₂CH₂)——

PCL-Poly-(ε-caprolactone) diol,
in which R is typically
——(CH₂CH₂)——

PEG-Poly-(ethylene glycol)

Examples of other polyols which may act as soft segments include poly-(4-hydroxybutyrate) diol (P4HB diol), poly-(3-hydroxybutyrate) diol (P3HB diol), polypropylene glycol and any copolymers thereof including PLGA dial, P(LA/CL) diol and P(3HB/4HB) diol.

Polymeric Scaffolds

Polyols with hydroxyl functionalities greater than 2 can be used when preparing thermoset (cross linked) polymers.

It has been found that the polyurethanes or polyurethane ureas according to the invention form porous and non-porous cross-linked or linear polymers which can be used as tissue engineering scaffolds. It has also been found that certain of the biodegradable polyurethanes or polyurethane ureas according to the invention exhibit a glass transition between room temperature and 37° C. This property can be used to extrude hard materials on FDM apparatus (going in at 20° C.) which will soften and even become elastomeric in vivo while groups cells on scaffolds in a bioreactor at physiological temperatures of 37° C. This is also a very useful property for soft tissue applications.

The polymers in both cross linked and linear form can be used to fabricate various types of scaffolds. For example, the linear polymers can be fabricated to form fibres using techniques such as reactive extrusion. The fibres can be woven or knitted to fabricate membranes useful in applications such as wound repair. Likewise, polymers in both form can be machined or lathed to form orthopaedic fixation scaffolds such as screws, pins, plates and spinal cages. Such devices are typically prepared by compression moulding the polymers as a solid or porous block and machined to form the appropriate scaffold structure.

The polyurethanes or polyurethane ureas can be sterilized without risk to their physical and chemical characteristics, preferably using gamma radiation to ensure sterility.

The polyurethanes or polyurethane ureas may incorporate biological and inorganic components selected for their ability to aid tissue repair in viva When cured, the polyurethanes or polyurethane ureas according to the invention form a biodegradable biocompatible scaffold which may be porous and contain interpenetrating polymer networks so as to enable the inclusion of biological and inorganic components. These biological and inorganic components which are preferably selected from the groups consisting of cells, progenitor cells, growth factors, other components for supporting cell growth, drugs, calcium phosphate, hydroxyapatite, hyaluronic acid, nonparticulate tricalcium phosphate and hydroxyapatite type fillers, radio opaque substances including barium sulfate and barium carbonate, adhesives including fibrin, collagen and transglutaminase systems, surfactants including siloxane surfactants, silica particles, powdered silica, hollow fibres which may be used to seed cells in the polyurethanes, and other porogens including for example, gelatin beads. The biological and inorganic components may be present in quantities according to need, especially in the case of the living additives such as cells and progenitor cells. Amounts of up to a least 20% w/w may be acceptable.

The scaffolds may preferably incorporate biological and inorganic components which are desirably selected from the group consisting of cells, progenitor cells, growth factors, other components for supporting cells growth, drugs, calcium phosphate, hydroxyapatite, hyaluronic acid, non particulate tricalcium phosphate and hydroxyapatite type fillers, adhesives including fibrin, collagen and transglutaminase systems, surfactants including siloxane surfactants, silica particles, powdered silica, hollow fibres which may be used to seed cells in the polyurethanes or polyurethane ureas, and other porogens including, for example, gelatin beads. The biological and inorganic components may be present in quantities according to need, especially in the case of the living additives such as cells and progenitor cells. Amounts of up to at least 20% w/w may be acceptable.

Preferably the cured scaffolds according to this aspect of the invention have a compressive strength in the range of 0.05-200 MPa The compressive strength of the scaffold will vary according to its porosity and according to the biological components added. Preferably the scaffolds have pores in the size range of 100-500 micron, more preferably 150-300 micron.

More preferably the porous scaffolds are seeded with living biological components or drugs selected so as to aid the tissue repair process in the patient being treated. The biological components so selected may be cells, progenitor cells, growth factors and other components for supporting cell growth. Suitable cells may include osteoblasts, chondrocytes, fibroblasts or other precursor cells. Suitable drugs are any which assist in the tissue engineering application of interest.

Preferably the scaffold is a biodegradable stent useful in treatment of coronary heart disease. In another aspect of the invention, the biodegradable biocompatible polyurethanes or polyurethane ureas of the invention are used as stent coatings in the treatment of coronary heart disease.

There is also provided a use of polyurethanes or polyurethane ureas according to the invention in tissue repair or engineering comprising inserting in a subject in need of such treatment a scaffold comprising a cross-linked or linear biocompatible biodegradable polyurethane or polyurethane urea according to the invention.

In the description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

DETAILED DESCRIPTION OF THE DRAWINGS

In the Examples, reference will be made to the accompanying drawings in which.

EXAMPLES

Example 1

Preparation of Glycolic Acid-1,3-Propanediol Ester Diol (GA-1,3-PD)

Step one—polycondensation or dehydration—56.7 g of glycolic acid was heated at 220° C. to remove water for 5 hours under nitrogen out gassing in a large round-bottomed flask equipped with a magnetic stirrer bead, a still-head sidearm and condenser to collect the water runoff. The resulting product was polyglycolic acid (PGA), a white solid polymer.

Step two—transesterification—To approximately 43 g of white solid PGA was added 283.6 g of 1,3-propane diol (five to one mole ratio) and the temperature set at 200° C. for a period of 17 hours and 30 minutes of transesterification. The glycolic acid ester diol was purified by fractional distillation as outlined below.

Step three—Purification by fractional distillation—The dimer-containing liquid was then heated on the Kugelrohr at 50° C. under vacuum (0.01-0.001 torr) to remove unreacted 1,3-propane diol and then the temperature was increased to 70° C. to distil the dimer. The dimer fraction was collected and then distilled a second time to remove any 1,3-propane diol present. The GA-1,3-PD was a white somewhat slurry-like solid. In total there was 53 g GA-1,3-PD dimer (53% yield).

The chemical structure and properties of the ester diol prepared are summarised in Table 1 below:

TABLE 1

Properties of GA-1,3-PD

Figure 1:
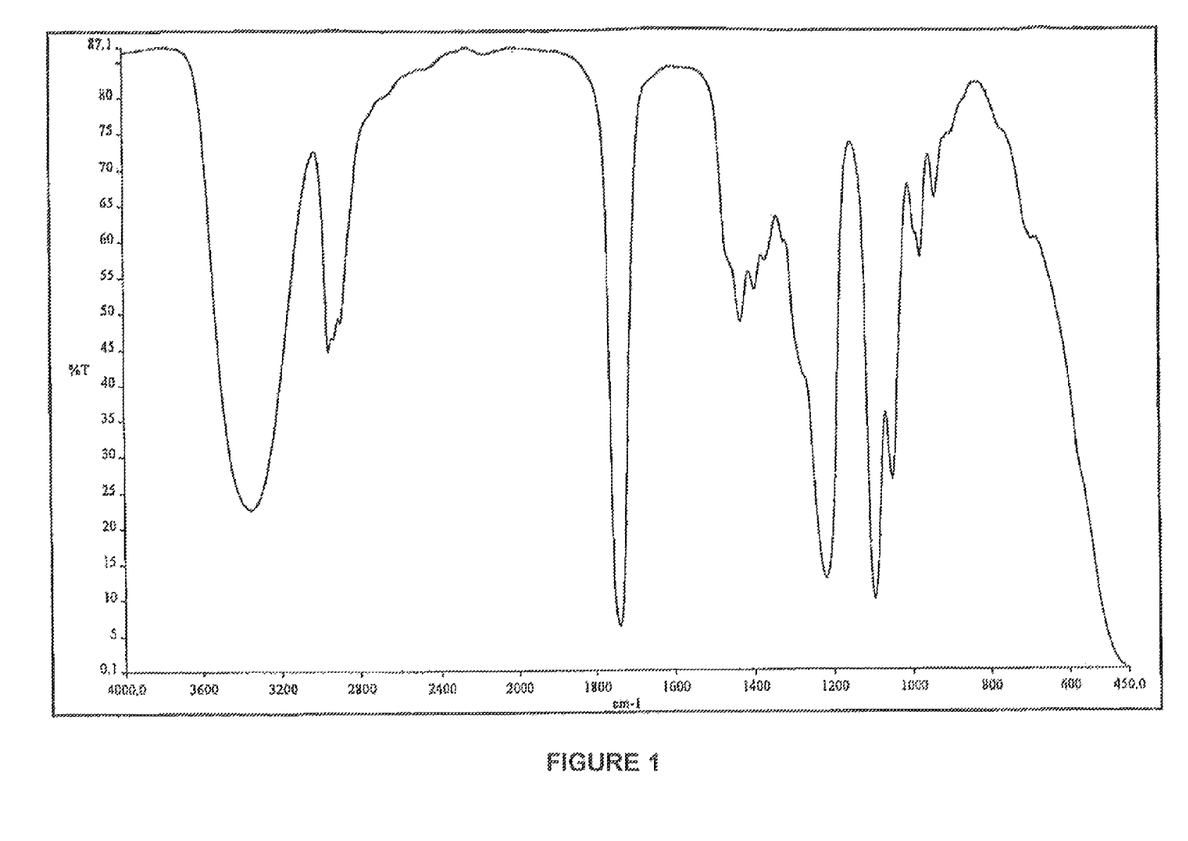
FIG. 1 is an IR Spectrum of GA-1,3-PD, NaCl plate.
Figure 2:
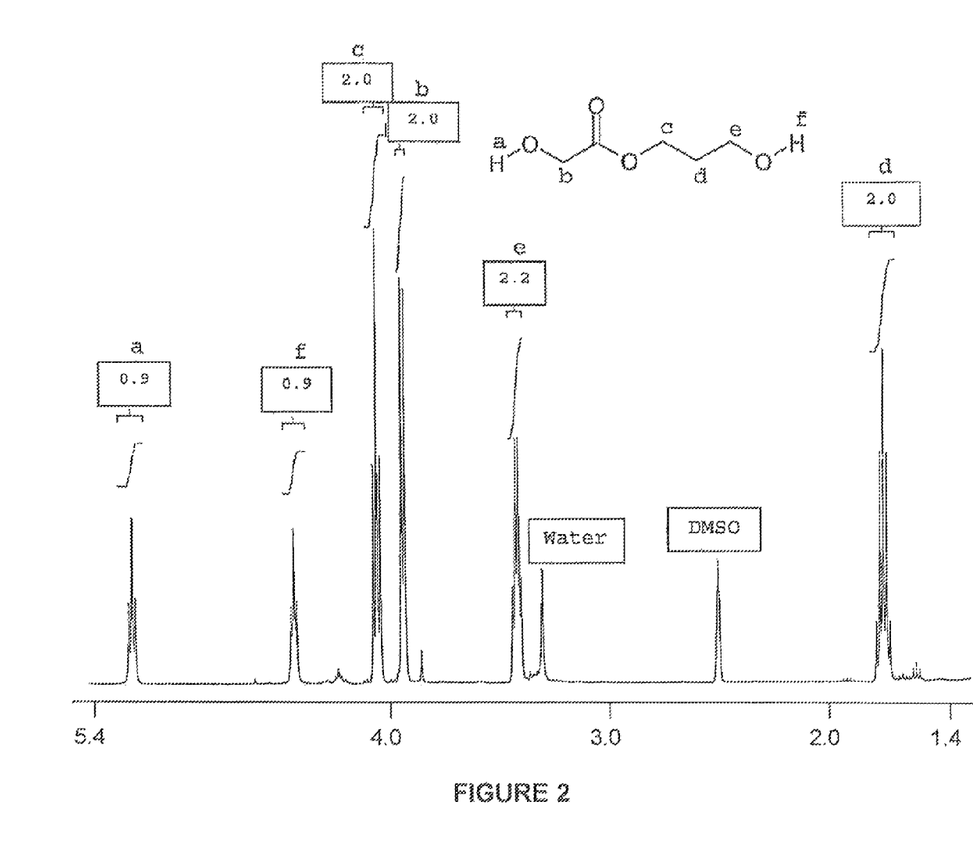
FIG. 2 is a $^1$HNMR Spectrum of GA-1,3-PD in deuterated DMSO.
Figure 3:
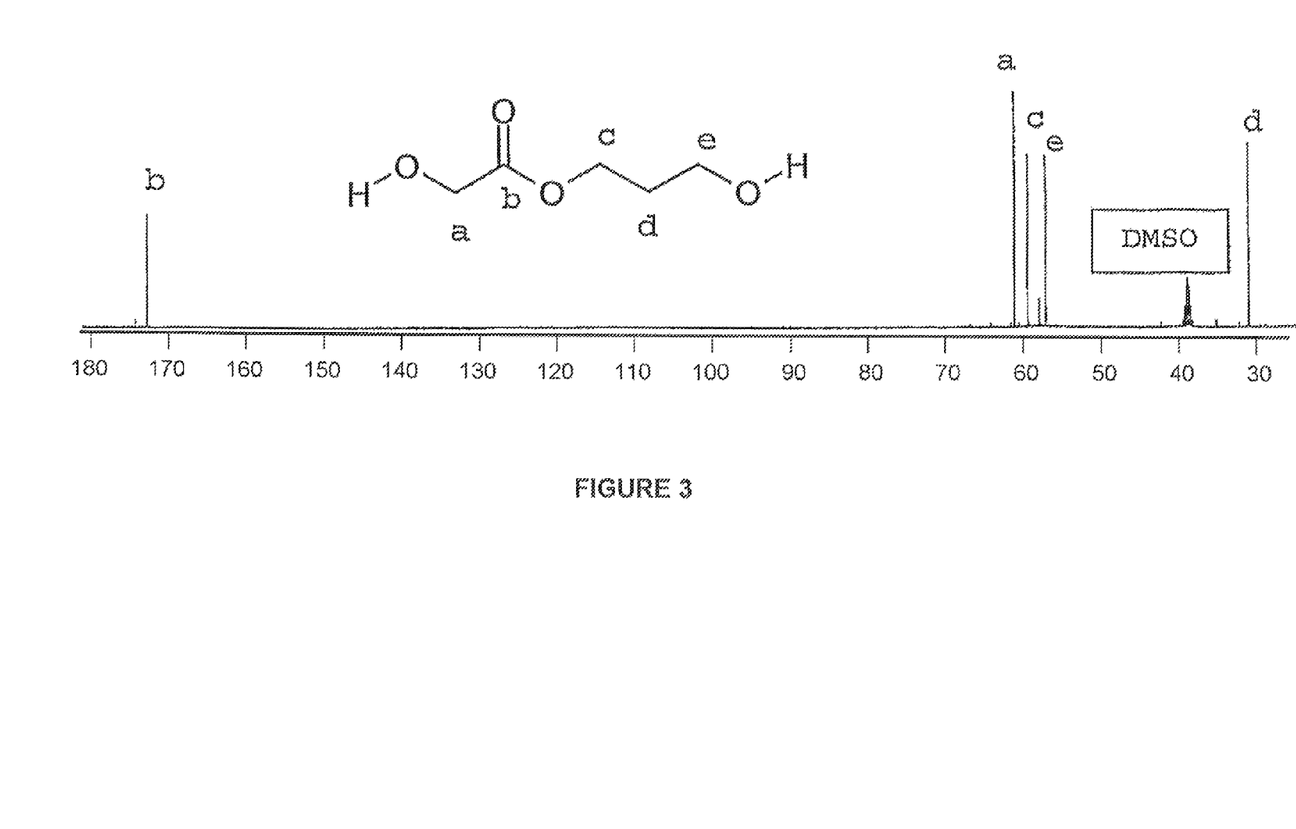
FIG. 3 is a $^{13}$CNMR Spectrum of GA-1,3-PD in deuterated DMSO.

| Abbreviation | Chemical Structure | Characterisation |
|---|---|---|
| GA-1,3-PD | (structure shown) | IR, $^1$HNMR, $^{13}$CNMR (FIGS. 1 to 3) |

Example 2

Preparation of Dicarboxylic Ester Diol Chain Extenders

Step one—Condensation—23.6 g of succinic acid (a diacid) was heated with 248 g of ethylene glycol (1:10 mole ratio) to 170° C. for 20 hours under nitrogen out gassing in a round-bottomed flask equipped with a magnetic stirrer bead, a still-head sidearm and condenser to collect the water runoff.

Step two—Purification by fractional distillation—The product from step one was then heated under vacuum (0.01 torr) on the Kugelrohr to remove ethylene glycol at 40-50° C. and then increased to 120° C. to distil the EG-Suc-EG trimer which came over as a colourless liquid. Yield was 22.7 g, (55.1% yield).

TABLE 2

Properties of dicarboxylic acid ester diols

| | Chemical Structure | Characterisation |
|---|---|---|
| EG-Suc-EG | (structure shown) | IR, $^1$HNMR, $^{13}$CNMR |
| EG-Fum-EG | (structure shown) | IR, $^1$HNMR, $^{13}$CNMR |

Example 3

Preparation of Polyurethanes Using Chain Extenders of Examples 1 and 2

Materials: Poly(ε-caprolactone), (PCL), soft segments (molecular weight 426) were dried at 90° C. for 4 hours under vacuum (0.1 torr). HDI (Aldrich) was used as received (colourless). Stannous octoate (Aldrich) was kept moisture free and used as received. The chain extender was synthesised and distilled then kept sealed, refrigerated and dry until use.

Method: A mixture of PCL soft segment diol (35,000 g), chain extender (21,311 g) and stannous octoate (0.050 g) were weighed into a 100 ml predried polypropylene beaker, covered with aluminium foil and heated to 70° C. under nitrogen in a laboratory oven. HDI (43,689 g) was weighed in a separate wet-tared predried polypropylene beaker and also heated to 70° C. The HDI was then added to the diol/EG/stannous octoate beaker and stirred manually until gelation occurred, at which time the hot viscous mixture was poured onto a Teflon® coated metal tray to cure at 100° C. for a period of about 18 hours. The resulting polymer was clear and colourless.

TABLE 3

Composition of polyurethanes containing degradable chain extenders

| Polyurethane | Hard segment % | Chain extender, (g) | HDI (g) | PCL-426 (g) | Stannous Octoate (g) |
|---|---|---|---|---|---|
| 1 | 65 | GA-1,3PD, 22.694 | 42.306 | 35.000 | 0.050 |
| 2 | 65 | EG-Suc-EG, 12.075 | 15.782 | 15.000 | 0.043 |
| 3 | 65 | EG-Fum-EG, 12.022 | 15.835 | 15.000 | 0.043 |
| 4* | 65 | EG, 9.696 | 36.732 | 25.000 | 0.071 |
| 5* | 35 | EG, 0.648 | 10.121 | 20.000 | 0.031 |

*Comparative polyurethanes formed using the non-degradable chain extender EG

Degradation was Conducted on 1 mm Thick Melt-Pressed Specimens in PBS Buffer pH7.4 for 3 Months at 37° C.

The method for degradation was as per ASTM International standard F 1635: Standard Test Method for In vitro Degradation Testing of Poly (L-lactic Acid) Resin and Fabricated Form for Surgical Implants. In short, the conditions were: Polymers were meltpressed to 100-200 μm thick and strips were cut 5 mm ×45 mm, buffer was 0.1M PBS pH 7.4, temperature was 37° C., solution:specimen ratio was between 100:1 and 300:1, 0.1% sodium azide was added as antimicrobial, samples were all placed in a 50 rpm agitated incubator, 6 specimens per material and only one specimen per jar.

TABLE 4

Mass loss and GPC molecular weights before and after degradation of the polyurethanes of Table 3

| PU | % Mass Loss | Pre Degradation | | | Post Degradation | | | % ΔMn |
|---|---|---|---|---|---|---|---|---|
| | | Mn | Mw | PD | Mn | Mw | PD | |
| 1 | 0.88 ± 0.1 | 28,096 | 46,838 | 1.67 | 18,596 | 31,122 | 1.67 | 66.2 |
| 2 | 2.82 ± 0.2 | 15,802 | 26,973 | 1.71 | 13,071 | 20,673 | 1.58 | 82.7 |
| 3 | 0.51 ± 0.2 | 34,123 | 91,025 | 2.67 | 19,281 | 38,163 | 1.98 | 56.5 |
| 4* | 0.42 ± 0.2 | 121,842 | 443,397 | 3.64 | 118,803 | 531,502 | 4.47 | 2.5 |
| 5* | 1.91 ± 0.2 | 16,953 | 29,660 | 1.75 | 16,920 | 29,013 | 1.71 | 0.2 |

Example 4

Preparation of CL-EG Dimer

ε-caprolactone (114.14 g) and ethylene glycol (310.35 g) were added to a round-bottomed flask and heated to 190° C. overnight with a vertical condenser to avoid loss of reagents.

Figure 4:
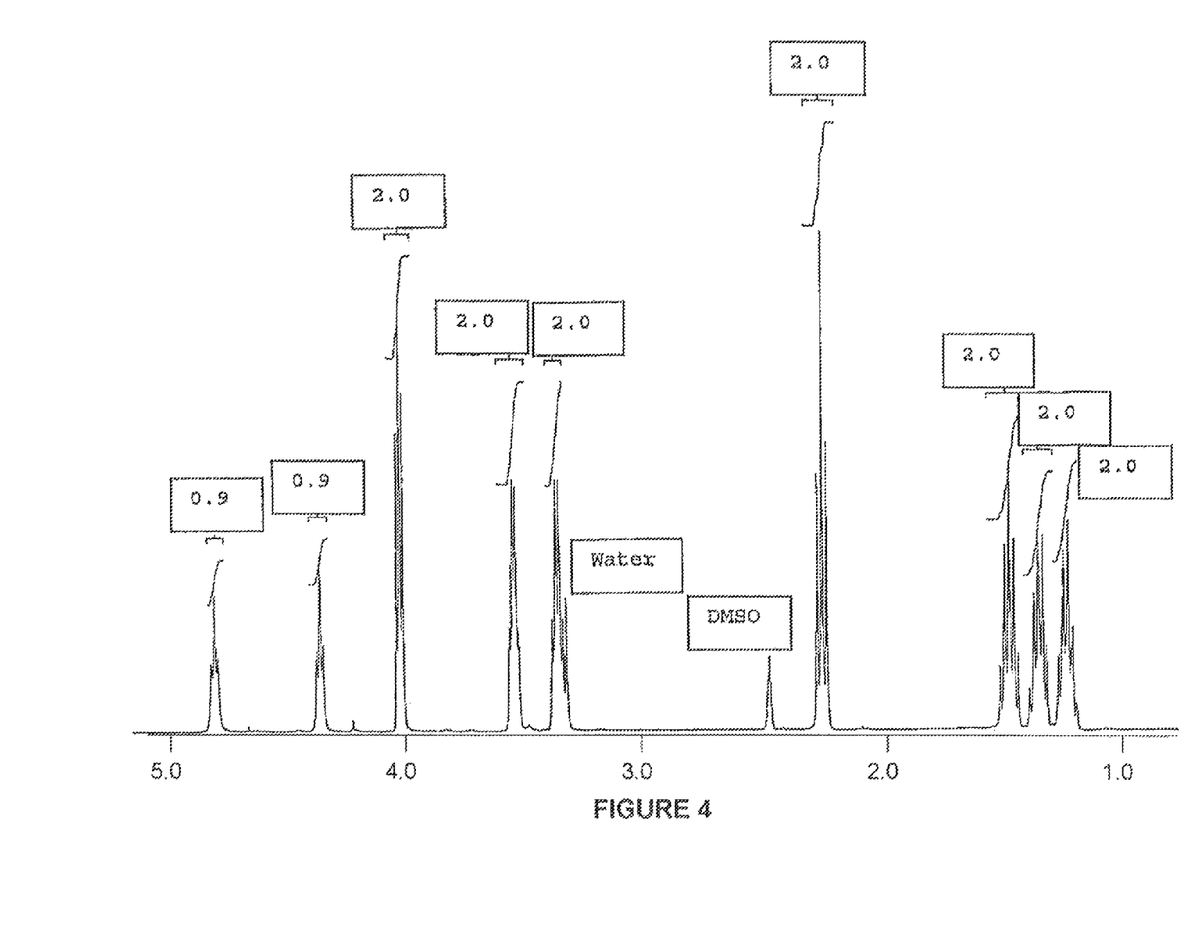
FIG. 4 is a $^1$HNMR Spectrum of CL-EG Dimer.

The ethylene glycol was removed on the Kugelrohr (0.01-0.001 torr) at 40-50° C. and then the CL-EG dimer was distilled at 100° C. CL-EG dimer was collected and this was redistilled to remove ethylene glycol, giving 120 g of CL-EG dimer. The dimer was a colourless low-viscosity liquid. Characterisation was by $^1$HNMR (FIG. 4).

Example 5

Preparation of CL-BDO Dimer

ε-caprolactone (79.83 g) and 1,4-butane diol (450.60 g) were added to a round-bottomed flask and heated to 180° C. over the weekend (~66 hours) with a vertical condenser to avoid loss of reagents.

Figure 5:
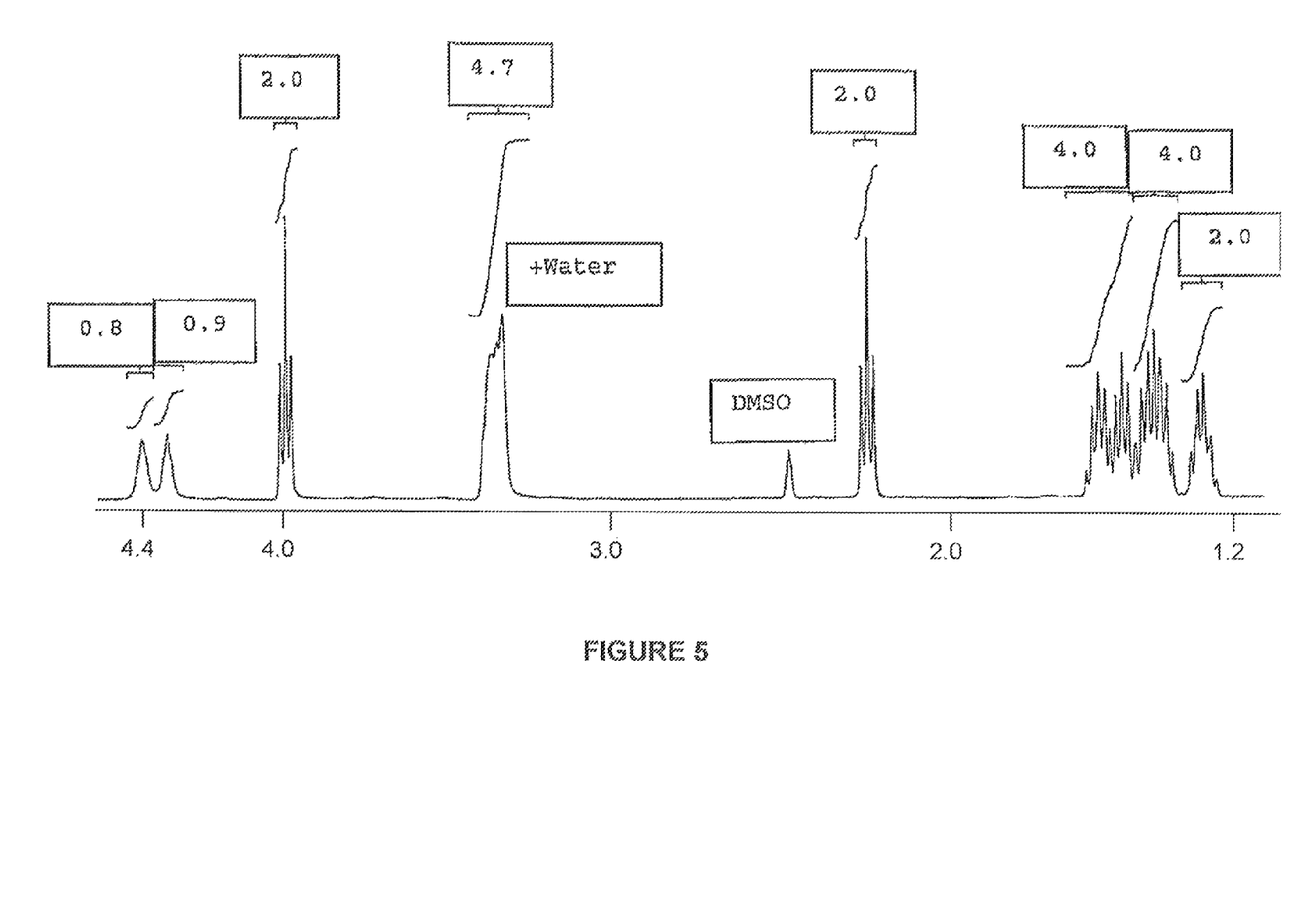
FIG. 5 is a $^1$HNMR Spectrum of CL-BDO Dimer.

The 1,4-butane diol was removed on the Kugelrohr (0.01-0.001 torr) at 80° C. and then the CL-BDO dimer was distilled at 110° C. CL-BDO dimer was collected and redistilled to remove BDO, giving 63.75 g of CL-BDO dimer. The dimer was a colourless low-viscosity liquid. Characterisation was by $^1$HNMR (FIG. 5).

Example 6

Comparative Jydrolysis at 100° C.

Two polymers from Table 3 can be compared for hydrolytic degradation at 100° C. and measured by change in concentration of amine in solution (due to urethane hydrolysis). Approximately 5 g of polymer is weighed out and placed in a round-bottomed flask. Distilled water is then added to the flask containing the sample such that the sample to water ratio is approximately 1:50 (to obtain concentrated degradation products). The round-bottomed flask is then placed in an oil bath set to 130° C. and refluxed for 24 hours with a vertical condenser. The degradation products are collected and subjected to the Ninhydrin Assay. Ninhydrin Assay: Ninhydrin Reagent Solution is obtained from Sigma, product code number N 7285. The protocol on the product information sheet is followed with regard to the assay as well as the preparation of the standard curve.

Example 7

Preparation of Cross Linked Polymers Incorporating Degradable Chain Extenders.

A prepolymer of pentaerythritol (PE) with ELDI (2.0 g) is weighed into a glass vial. Degassed and dried dimer from Table 3 0.461 g (MW 120) is added to the prepolymer. The mixture is manually stirred using a spatula for 3 minutes with stannous 2-ethyl hexanoate catalyst (0.002 g, 0.1% based on based on total weight of prepolymer) and is degassed under a vacuum for 5 min. The viscous mixture is taken into a 2.5 ml syringe and dispensed 0.33 g into each cylindrical cavity (6 mm D×12 mm L) in a multi-cavity Teflon mould and cured overnight at 38° C. to give cylindrical polymer test specimens. A second polymer is prepared by incorporating 5 wt-% of β-tricalcium phosphate (TCP, 5 micron particle size). TCP is added to the reactant mixture and stirred using a high speed mechanical stirrer for uniform distribution.

The cured polymer samples is tested using Instron (Model 5568) for compressive strength and modulus according to ASTM method F451-756.

Example 8

Materials: Poly(ethylene glycol) (PEG) (molecular weight 1000) is dried at 90° C. for 4 hours under vacuum (0.1 torr). HDI (Aldrich) is used as received. Stannous octoate (Aldrich) is kept moisture free and used as received. The chain extender is synthesised using the procedure described in Example 1. The distilled product is kept sealed under refrigerated and dry conditions until use.

Method: The polymer is prepared using the method described in Example 3. A mixture of polyethylene glycol (10,000 g), chain extender (1.713 g), EG (1.330 g) and stannous octoate (0.010 g) are weighed into a 100 ml predried polypropylene beaker, covered with aluminium foil and heated to 70° C. under nitrogen in a laboratory oven. HDI (7.862 g) is weighed in a separate wet-tared predried polypropylene beaker and heated to 70° C. HDI is then added to the polyol/chain extender mixture in a beaker and stirred manually for 3 min. The viscous mixture is then poured onto a Teflon® coated metal tray and cured at 100° C. for a period of about 18 hours in a nitrogen circulating oven.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

The invention claimed is:

1. A biocompatible biodegradable polyurethane or polyurethane urea comprising a segment formed from a chain extender, wherein the chain extender is a compound of formula (1) or formula (2):

(1)

(2)

wherein $R_1$, $R_2$ and $R_3$ are independently selected from $C_{1-20}$ alkylene and $C_{2-20}$ alkenylene, at least one of which is substituted by more than one group selected from the group consisting of $C_{1-6}$ alkyl, $C_{2-6}$ alkenyl, $C_{2-6}$ alkynyl, aryl, halo, halo $C_{1-6}$ alkyl, halo $C_{2-6}$ alkenyl, halo $C_{2-6}$ alkynyl, haloaryl, hydroxy, $C_{1-6}$ alkoxy, $C_{2-6}$ alkenyloxy, $C_{1-6}$ aryloxy, benzyloxy, halo $C_{1-6}$ alkoxy, haloalkenyloxy, haloaryloxy, nitro, nitro$C_{1-6}$ alkyl, nitro$C_{2-6}$ alkenyl, nitro$C_{2-6}$ alkynyl, nitroaryl, nitroheterocyclyl, amino, $C_{1-6}$ alkylamino, $C_{1-6}$ dialkylamino, $C_{2-6}$ alkenylamino, $C_{2-6}$ alkynylamino, arylamino, diarylamino, benzylamino, dibenzylamino, acyl, alkenylacyl, alkynylacyl, arylacyl, acylamino, diacylamino, acyloxy, $C_{1-6}$ alkylsulphonyloxy, arylsulphenyloxy, heterocyclyl, heterocyclyloxy, heterocyclylamino, haloheterocyclyl, $C_{1-6}$ alkylsulphenyl, arylsulphenyl, carboalkoxy, carboaryloxy, mercapto, $C_{1-6}$ alkylthio, benzylthio, acylthio and phosphorus-containing groups.

2. A biocompatible biodegradable polyurethane or polyurethane urea according to claim 1 wherein the aryl group is selected from the group consisting of phenyl, naphthyl, tetrahydronaphthyl, indane and biphenyl.

3. A biocompatible biodegradable polyurethane or polyurethane urea according to claim 1 wherein the heterocyclyl group is selected from the group consisting of unsaturated 3 to 6-membered heteromonocyclic groups containing 1 to 4 nitrogen atoms, saturated 3 to 6-membered heteromonocyclic groups containing 1 to 4 nitrogen atoms, unsaturated condensed heterocyclic groups containing 1 to 5 nitrogen atoms, unsaturated 3 to 6-membered heteromonocyclic groups containing an oxygen atom, unsaturated 3 to 6-membered heteromonocyclic group containing 1 to 2 sulphur atoms, unsaturated 3 to 6-membered heteromonocyclic group containing 1 to 2 oxygen atoms and 1 to 3 nitrogen atoms, saturated 3 to 6-membered heteromonocyclic group containing 1 to 2 oxygen atoms and 1 to 3 nitrogen atoms, unsaturated condensed heterocyclic group containing 1 to 2 oxygen atoms and 1 to 3 nitrogen atoms, unsaturated 3 to 6-membered heteromonocyclic group containing 1 to 2 sulphur atoms and 1 to 3 nitrogen atoms, saturated 3 to 6-membered heteromonocyclic group containing 1 to 2 sulphur atoms and 1 to 3 nitrogen atoms, and unsaturated condensed heterocyclic group containing 1 to 2 sulphur atoms and 1 to 3 nitrogen atoms.

4. A biocompatible biodegradable polyurethane or polyurethane urea according to claim 1 wherein the heterocyclyl group is selected from the group consisting of pyrrolyl, pyrrolinyl, imidazolyl, pyrazolyl, pyridyl, pyrimidinyl, pyrazinyl, pyridazinyl, triazolyl, tetrazolyl, pyrrolidinyl, imidazolidinyl, piperidino, piperazinyl, indolyl, isoindolyl, indolizinyl, benzimidazolyl, quinolyl, isoquinolyl, indazolyl, benzotriazolyl, tetrazolopyridazinyl, pyranyl or furyl, thienyl, oxazolyl, isoxazolyl, oxadiazolyl, morpholinyl, benzoxazolyl, benzoxadiazolyl, thiazolyl, thiadiazolyl, thiazolidinyl, benzothiazolyl and benzothiadiazolyl.

5. A biocompatible biodegradable polyurethane or polyurethane urea according to claim 1 wherein at least one of the substituents of the $C_{1-20}$ alkylene or $C_{2-20}$ alkenylene groups of $R_1$, $R_2$ or $R_3$ comprises a bioactive moiety.

6. A biocompatible biodegradable polyurethane or polyurethane urea according to claim 1 wherein the chain extender of formula (1) is prepared by a process which comprises the step of transesterification of a compound of formula (3) or (4):

(3)

(4)

wherein n is an integer from 1 to 50;

with a compound of formula $HOR^1OH$.

7. A biocompatible biodegradable polyurethane or polyurethane urea according to claim 1 comprising the chain extender of formula (1) or formula (2) and another chain extender.

8. A biocompatible biodegradable polyurethane or polyurethane urea according to claim 7, in which the other chain extender is a diol, dithiol, diamine, amino acid or dicarboxylic acid.

9. A biocompatible biodegradable polyurethane or polyurethane urea according to claim 1 which comprises a reaction product of an isocyanate, polyol and a chain extender.

10. A biocompatible polyurethane or polyurethane urea according to claim 9 in which the polyurethane or polyurethane urea is thermoplastic and of the general formula:

in which $R_x$ is from the isocyanate, $R_y$ is from the chain extender and $R_z$ is from the soft segment polyol;

'q' is the average number of repeat units in the hard segment;

'r' is the average number of repeat units in the soft segment; and

's' is proportional to the molecular weight of the polymer and includes both the hard segments repeat units and the soft segment;

and in which 'q' is an integer between 1 and 100, 'r' is an integer between 0 and 100, and 's' is an integer between 1 and 500.

11. A biocompatible polyurethane or polyurethane urea according to claim 9, in which the isocyanate is a diisocyanate.

12. A biocompatible polyurethane or polyurethane urea according to claim 9, in which the polyol is a diol, triol, tetrol, hexol or macrodiol.

13. A biocompatible polyurethane or polyurethane urea according to claim 9, in which the polyol is terminated by a hydroxyl, thiol or carboxylic acid group.

14. A biocompatible polyurethane or polyurethane urea according to claim 9, wherein the polyol is of general formula:

wherein h and/or k are independently 0 or an integer, j is an integer, Z is a linear or branched alkyl, alkenyl or aryl wherein each occurrence of Z independently within the segment j may be the same or different and R is a linear or branched alkyl, alkenyl, aminoalkenyl, alkoxy or aryl function wherein each occurrence of R independently within the segments h or k may be the same or different, and wherein one or both of R and Z optionally comprises a bioactive moiety.

15. A biocompatible polyurethane or polyurethane urea according to claim 14, in which the polyol is selected from the group consisting of poly(ε-caprolactone) diol, MW 400: in which Z is ($CH_2$—$CH_2$), R is $(CH_2)_5$ and j =1 and (h+k)=2.96;

(glycolic acid—ethylene glycol) dimer: in which Z is ($CH_2$—$CH_2$), R is ($CH_2$), j =1 and (h+k)=1; and poly(ethylene glycol), MW 400: in which h=0, k=0, j=~13 and $R^6$ is ($CH_2$—$CH_2$).

16. A biocompatible polyurethane or polyurethane urea according to claim 9, in which the polyol has a molecular weight of 200-5000, 200-2000 or 200-1000.

* * * * *